Sept. 30, 1969 P. ECKE Plant Pat. 2,923
POINSETTIA PLANT
Filed Feb. 27, 1968
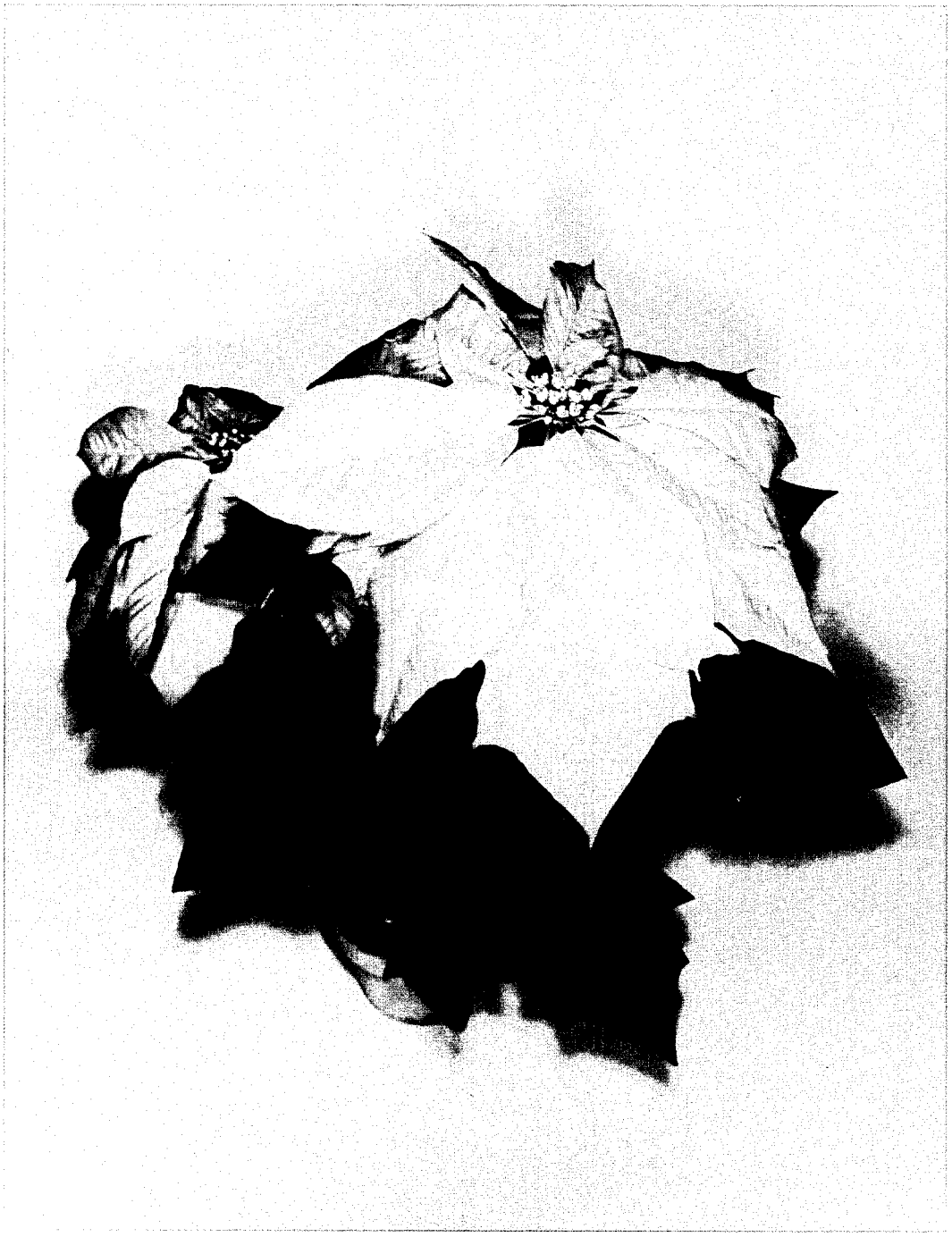
Inventor.
Paul Ecke
By: Robb & Robb
Attorneys.

United States Patent Office

Plant Pat. 2,923
Patented Sept. 30, 1969

2,923
POINSETTIA PLANT

Paul Ecke, Encinitas, Calif., assignor to Paul Ecke, Inc., Encinitas, Calif., a corporation of California Filed Feb. 27, 1968, Ser. No. 708,728
Int. Cl. A01h 5/12
U.S. Cl. Plt.—86 1 Claim The present invention relates to a new and distinct variety of poinsettia plant (botanically known as *Euphorbia pulcherrima*), which was originated by me by crossing two unnamed and unpatented red poinsettia seedlings.

The primary objectives of this breeding were to produce a new and improved poinsettia variety which has stiff stems that do not require staking, wider bracts than other varieties heretofore known in commerce, a compact inflorescence form which creates an attractive effect in each bloom, and which retains its foliage and bracts for an unusually long period of time after reaching maturity. These objectives were fully achieved, along with other desirable improvements as evidenced by the following unique combination of characteristics which are outstanding in the new variety and which distinguish it from its parents, as well as from all other varieties of which I am aware:

(1) A very vigorous, tough, and durable plant habit, with the plant being of medium height and having the ability to grow well as a multiple stem and multiple bloom plant;

(2) A very vigorous and extensive root system;

(3) Stiff stems which do not require staking;

(4) Many very wide bracts of a distinctive shape and arrangement that give the plant a full and complete appearance;

(5) Retention of the bracts, foilage and inflorescences for an unusually long period of time after reaching maturity;

(6) A habit of not requiring light to delay bud set;

(7) A habit of setting buds quite easily under higher night temperatures and longer day lengths than other poinsettia varieties;

(8) A well-pinching habit which produces 3 or more breaks;

(9) A normally later blooming habit, but having the ability to be satisfactorily brought into bloom and full maturity in every month of the year through the exercise of proper greenhouse cultural techniques;

(10) A distinctive and attractive, slightly ruffled appearance of the bracts and their absence of any tendency to droop with age;

(11) A distinctive and attractive general color tonality of the bracts corresponding to near Cardinal Red;

(12) Absence of drooping and retention of the inflorescence position relative to the bracts without rising as occurs in other varieties as the inflorescence approaches maturity; and

(13) Excellent keeping qualities and consequent suitability for home decoration.

Asexual reproduction of my new variety by vegetative cuttings propagated under mist at Encinitas, Calif., shows that the foregoing characteristics and distinctions come true to form and are established and transmitted through succeeding propagations.

The accompanying drawing shows a typical specimen plant of my new variety as depicted in color as nearly true as it is reasonably possible to make the same in a color illustration of this character.

The following is a detailed description of my new poinsettia variety, with color terminology in accordance with Wilson's Horticultural Colour Chart, except where general color terms of orginary dictionary significance are obvious, as based on specimens grown at Encinitas, Calif., under regular commercial practices:

Parentage: Seedling.

*Seed parent.*—An unnamed and unpatented red seedling.

*Pollen parent.*—An unnamed and unpatented red seedling.

Propagation: Holds its distinguishing characteristics through succeeding propagation by vegetative cuttings.

Form: Medium tall; upright; graceful contour.

Habit of growth: Vigorous grower but not too tall.

Rooting habit: Very fast (from 12 to 15 days under mist); vigorous; extensive; uniform.

Blooming habit: Approximately 10 to 11 weeks after start of short days.

Blooming season: Naturally in December, but has excellent suitability for forcing in every month of the year by appropriate greenhouse culture practices.

Foliage: Alternate; borne horizontally on stems; persistent; normal abundance.

*Size.*—Medium; borne on short petioles; from about 3 inches to 6 inches long; from about 2½ inches to 5 inches wide.

*Shape.*—Little serration; wide at base and abruptly tapering to long point at tip.

*Texture.*—Upper side—medium glossy; medium smooth; with ordinary recessed veins. Under side—Dull; with ordinary protruding veins.

*Margin.*—Well defined.

*Color.*—New foliage: upper side—near Scheele's Green, Plate 860, page 175; lower side—near Scheele's Green, Plate 860/1, page 175. Old foliage: upper side—near Ivy Green, Plate 0001060, page 200; lower side—near Leek Green, Plate 000858, page 197.

Disease resistance: Resistant to rhizoctonia and pythium stem and root rot during propagation and growing period, and very resistant to botrytis during blooming period, as determined by comparison with other plants grown under the same cultural conditions at Encinitas, Calif., which are infected with these diseases.

Bracts: Many (approximately 15 to 20 in number); very wide; excellent retention; new bracts form and develop as other bracts mature; very long lasting qualities; short pointed when young, but becoming long pointed at maturity; retain relative position and do not droop when mature or as bracts continue to age; retain their color exceptionally well; slightly ruffled in appearance; have short petioles giving a full appearance; tight center giving inflorescence form which creates an attrative appearance. Color:upper side—near Cardinal Red, Plate 822/3, page 168; under side—near Rose Opal, Plate 022/1, page 110.

Flowers:

*Borne.*—Continuously for several months; many flowers per stem in regular clusters in varying stages of development; borne on strong, very short stems; slow development, giving a compact appearance for a greater period of time; position of the flowers remain relatively low without rising as it does in other commercial poinsettia varieties during early development, and does not spread out during later stages of development, thereby giving a more attractive appearance for a longer period of time.

*Quality of bloom.*—Relatively abundant; continuous flowers gradually drop off after maturity; flower clusters remain tight but new ones do not continue to develop; centers do not spread.

*Buds.*—From medium to large size; borne on light green stems. Color—near Lettuce Green, Plate 861/3, page 176.

Reproductive organs:

*Stamens.*—Few; from ⅛ inch to ¼ inch long. Color—near Claret Rose, Plate 021, page 109.

*Pollen.*—Color—near Naples Yellow, Plate 403, page 121.

*Styles.*—Color—near Rose Opal, Plate 022, page 110.

*Ovaries.*—Color—near Lettuce Green, Plate 022, page 110.

*Nectar cups.*—Near Egyptian Buff, Plate 407, page 122.

General observations. As compared with its unnamed red seed parent, the new variety principally differs from this parent in that it is shorter and the color of the bracts of the new variety are a lighter red than that of this parent. In comparison with its unnamed pollen parent, the new variety principally differs from this parent in that the bracts are much wider than the bracts of this parent.

I claim:

1. A new and distinct variety of poinsettia plant, substantially as herein shown and described, characterized particularly as to novelty by the unique combination of a very vigorous, tough, and durable plant habit, with the plant being of medium height and having the ability to grow well as a multiple stem and multiple bloom plant, a very vigorous and extensive root system, stiff stems which do not require staking, many very wide bracts of a distinctive shape and arrangement that give the plant a full and complete appearance, retention of the bracts, foliage and inflorescences for an unusually long period of time after reaching maturity, a habit of not requiring light to delay bud set, a habit of setting buds quite easily under higher night temperatures and longer day lengths than other poinsettia varieties, a well-pinching habit which produces 3 or more breaks, a normally later blooming habit, but having the ability to be satisfactorily brought into bloom and full maturity in every month of the year through the exercise of proper greenhouse cultural techniques, a distinctive and attractive, slightly ruffled appearance of the bracts and their absence of any tendency to droop with age, a distinctive and attractive general color tonality of the bracts corresponding to near Cardinal Red, absence of drooping and retention of the infloresence position relative to the bracts without rising as occurs in other varieties as the influorescence approaches maturity, and excellent keeping qualities and consequent suitability for home decoration.

No references cited.

ROBERT E. BAGWILL, Primary Examiner